United States Patent
Lindblad et al.

(10) Patent No.: US 10,865,170 B2
(45) Date of Patent: Dec. 15, 2020

(54) PROCESS FOR PRODUCING 2-BUTANOL FROM GAMMAVALEROLACTONE

(71) Applicant: Neste Oyj, Espoo (FI)

(72) Inventors: Marina Lindblad, Porvoo (FI); Mats Käldström, Porvoo (FI); Susanna Wallenius, Porvoo (FI); Kaisa Lamminpää, Porvoo (FI)

(73) Assignee: NESTE OYJ, Espoo (FI)

( * ) Notice: Subject to any disclaimer, the term of this patent is extended or adjusted under 35 U.S.C. 154(b) by 0 days.

(21) Appl. No.: 16/508,777

(22) Filed: Jul. 11, 2019

(65) Prior Publication Data

US 2020/0017430 A1  Jan. 16, 2020

(30) Foreign Application Priority Data

Jul. 13, 2018 (FI) .................................... 20185642

(51) Int. Cl.
*C07C 29/149* (2006.01)
*C07C 31/12* (2006.01)

(52) U.S. Cl.
CPC ............ *C07C 29/149* (2013.01); *C07C 31/12* (2013.01)

(58) Field of Classification Search
CPC ..................................................... C07C 29/149
USPC ......................................................... 568/881
See application file for complete search history.

(56) References Cited

U.S. PATENT DOCUMENTS 5,883,266 A  3/1999  Elliott et al.

FOREIGN PATENT DOCUMENTS

JP  2018070523 A  5/2018

OTHER PUBLICATIONS

Rozenblit et al: "Reaction mechanism of aqueous-phase conversion of [gamma]-valerolactone (GVL) over a Ru/C catalyst", Journal of Energy Chemistry, vol. 25, No. 6, pp. 1008-1014, 2016.*

(Continued)

*Primary Examiner* — Deborah D Carr
(74) *Attorney, Agent, or Firm* — Buchanan Ingersoll & Rooney PC

(57) ABSTRACT

A process is disclosed for selectively producing 2-butanol from GVL by using at least one transition metal catalyst selected from the group consisting of iron, ruthenium, cobalt, rhodium and iridium.

20 Claims, 2 Drawing Sheets

(56) References Cited

OTHER PUBLICATIONS

Figure 1A:
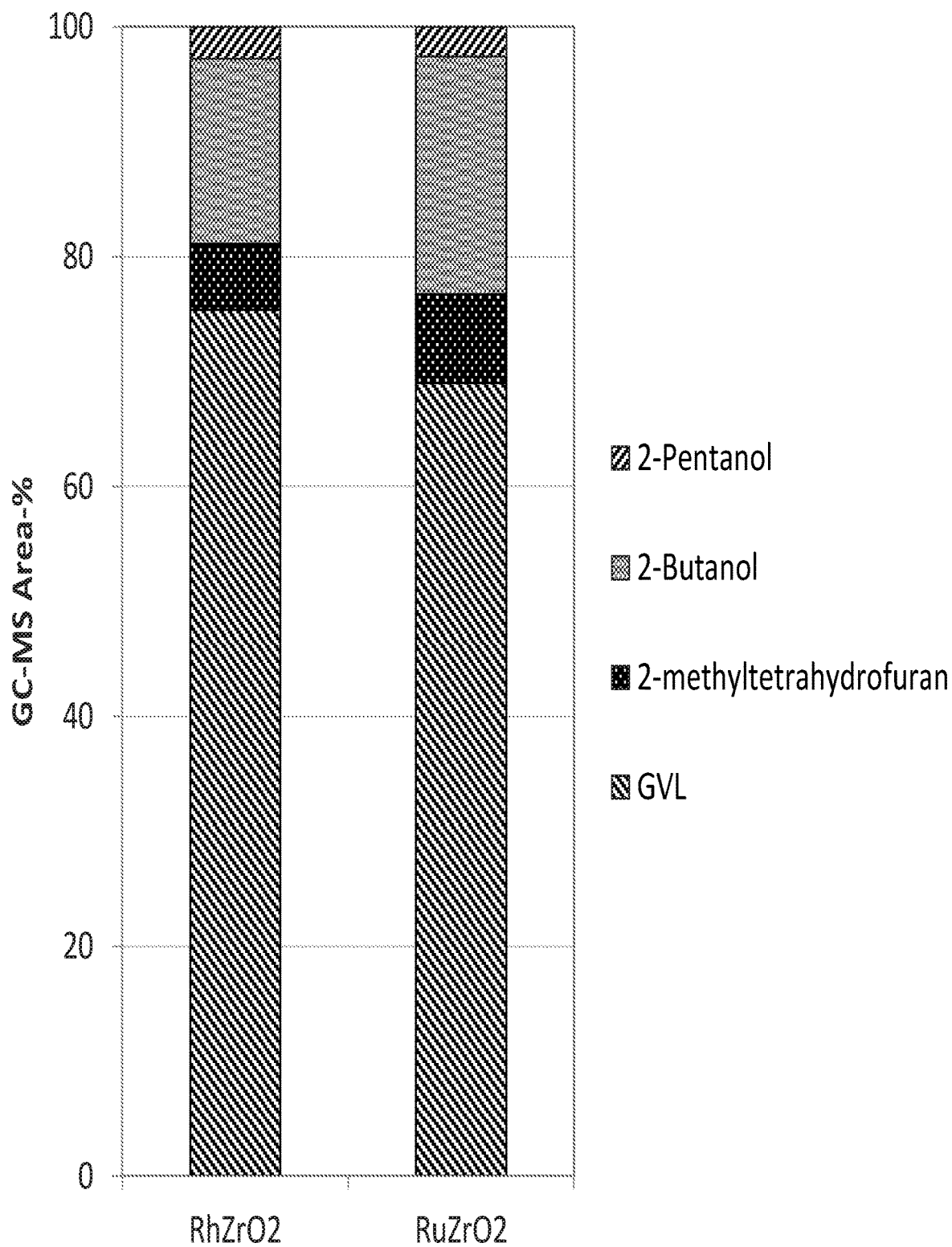

Jinkun et al: "Catalytic conversion of biomass-derived levulinic acid into alcohols over nanoporous Ru catalyst", Catalysis Science & Technology, vol. 8, No. 4, pp. 975-979, 2018.*
Jinku LV, et al., "Catalytic Conversion of Biomass-derived Levulinic Acid Into Alcohols Over Nanoporous Ru Catalyst", Catalysis Science & Technology, Jan. 1, 2018, pp. 975-979, vol. 8, No. 4.
The extended European Search Report dated Nov. 19, 2019, by the European Patent Office in corresponding European Application No. 19184107.1. (8 pages).
Al-Shaal et al., "Solvent-free-γ-valerolactone hydrogenation to 2-methyltetrahydrofuran catalyzed by Ru/C: a reaction network analysis", Green Chemistry, 2014, pp. 1358-1364.
Bababrik et al., "Reaction Mechanism for the Conversion of γ-Valerolactone (GVL) over a Ru Catalyst: A First-Principles Study", I&EC Research, vol. 56, No. 12, 2017, pp. 3217-3222.
Finnish Search Report dated Nov. 1, 2018.
Rozenblit et al., "Reaction mechanism of aqueous-phase conversion of γ-valerolactone (GVL) over a Ru/C catalyst", Journal of Energy Chemistry, vol. 25, 2016, pp. 1008-1014.
Yan et al., "Catalytic reactions of gamma-valerolactone: a platform to fuels and value-added chemicals", Applied Catalysis B: Environmental, vol. 179, 2015, pp. 292-304.

\* cited by examiner

PROCESS FOR PRODUCING 2-BUTANOL FROM GAMMAVALEROLACTONE

FIELD OF THE INVENTION

The present invention relates to selective production of 2-butanol from γ-valerolactone (GVL) with a catalyst.

BACKGROUND

2-Butanol (sec-butanol, sec-butyl alcohol, methyl ethyl carbinol; $C_4H_{10}O$) is a colourless solvent with a characteristic alcohol odor. It is only moderately miscible with water but is miscible in all proportions with many organic solvents.

2-Butanol is produced commercially by the indirect hydration of fossil C-4 streams, usually n-butene. In production, butadiene and isobutylene are removed from the C-4 stream and the remaining butanes-butylenes stream (raffinate-2), usually rich in butene-2, is reacted with sulphuric acid. Addition of water hydrolyses the resulting sec-butyl hydrogen sulphate and di-sec-butyl sulphate to 2-butanol and sulphuric acid; di-sec-butyl ether is a by-product of side reactions.

Most of the industrially produced 2-butanol is used to make methyl ethyl ketone, which is used in surface coatings, adhesives, lube oil dewaxing, magnetic tape manufacture, printing inks, and in chemical uses. A minor amount of 2-butanol is employed as a direct solvent, as well as in blends with aromatic hydrocarbons, ketones and other alcohols. 2-Butanol is also used as an intermediate for manufacturing chemicals that are used for solvent applications, such as blended with aromatic hydrocarbons, ketones, and other alcohols for use as a solvent for nitrocellulosic and acrylic lacquers, and as a coupling agent for applications in hydraulic brake fluids, industrial cleaning compounds, and paint remover. 2-Butanol is also used as a raw material in the manufacture of sec-butyl acetate and in the production of a xanthate derivative that is a collector in ore flotation. Other uses include the manufacture of perfumes, fruit essences, dyestuffs, and wetting agents.

The 2-butanol synthesis route described above is based on fossil sources. Hence, for renewable fuels and chemicals use of fossil 2-butanol is problematic because of its fossil origin, and renewable 2-butanol would be desirable for such uses.

It is thus an object of the present invention to provide a method for selectively producing 2-butanol from a renewable feedstock.

SUMMARY

According to the first aspect is provided a process for selective production of 2-butanol from γ-valerolactone (GVL) comprising:
  a. Providing in a reactor at least one transition metal catalyst selected from the group consisting of iron, ruthenium, cobalt, rhodium and iridium;
  b. Heating a feedstock containing GVL, thereby forming a heated GVL feedstock;
  c. Forming a reaction mixture by feeding into the reactor:
    i. The heated GVL feedstock; and
    ii. Hydrogen gas; and
  d. Maintaining the temperature of the reaction mixture in the range 200-300° C. to allow selective production of reaction products comprising 2-butanol.

An advantage of the present process is that an effective and selective process for producing 2-butanol from a renewable feedstock in a controlled manner is achieved. With the present invention it is possible to use GVL derived from a lignocellulosic source to produce 2-butanol and co-products. Thus, drawbacks relating to fossil raw materials can be avoided.

According to the second aspect is provided a use of a catalyst comprising at least one transition metal selected from the group consisting of iron, ruthenium, cobalt, rhodium and iridium, in a selective production of 2-butanol from GVL.

According to another aspect is provided a use of a catalyst comprising at least one transition metal selected from the group consisting of iron, cobalt, rhodium and iridium, in a selective production of 2-butanol from GVL.

An advantage of present use is high selectivity of 2-butanol production, and possibility to control co-product production by process conditions.

FIGURES

Figure 1B:
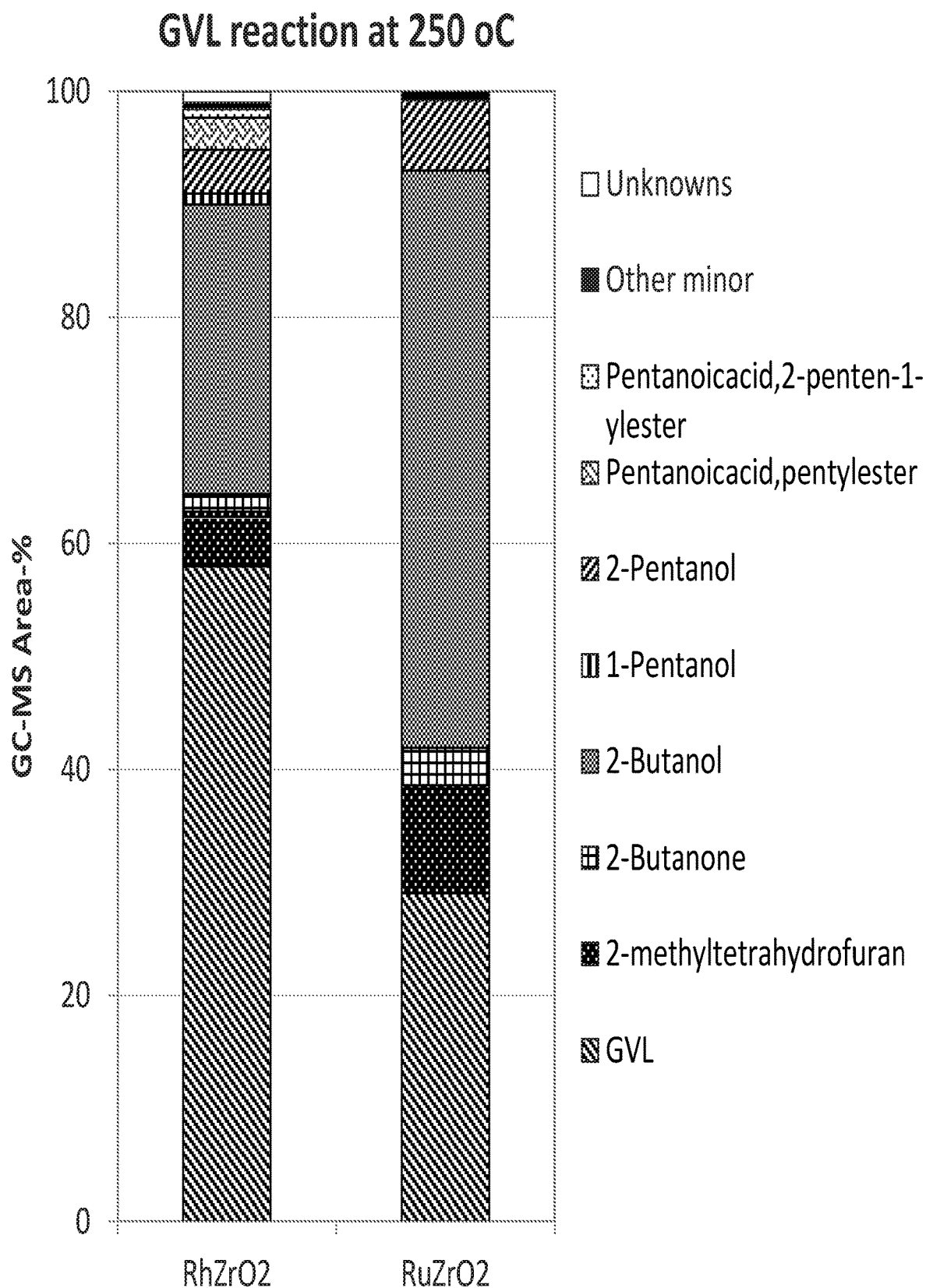

FIGS. 1A and 1B show product distribution (according to GC-MS) in GVL hydrogenation experiments over Rh/$ZrO_2$ and Ru/$ZrO_2$ catalysts for liquid products obtained at 225 and 250° C.

DETAILED DESCRIPTION OF THE INVENTION

As used herein, the term "comprising" includes the broader meanings of "including", "containing", and "comprehending", as well as the narrower expressions "consisting of" and "consisting only of".

In an embodiment the selectivity of 2-butanol production is at least 50% analysed as GC-MS area-%.

With the obtained high selectivity of 2-butanol production it is possible to decrease formation of co-products and to have a process, which provides primarily 2-butanol as the reaction product. Thus, in an embodiment the present process can be optimised for 2-butanol production, which is advantageous when co-products are not desired.

Scheme 1 shows a simplified reaction scheme according to the invention, which depicts part of the compounds formed from GVL by the present selective hydrogenation. Compounds derived from pentanoic acid—also a hydrogenation product from GVL—are not included as they are of minor importance for the Rh- and Ru-catalysts.

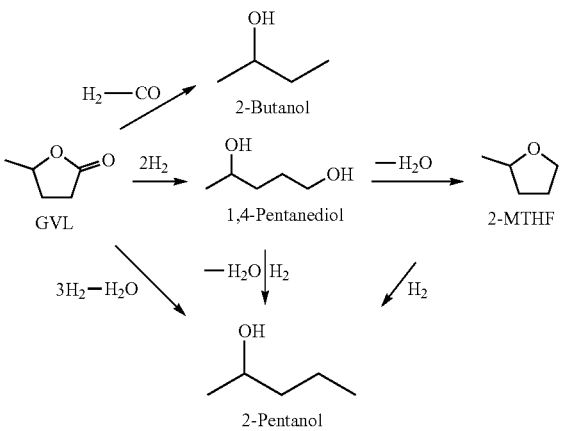

Scheme 1. Selective hydrogenation products from GVL.

GC-MS area-% can be calculated as follows: the relative amount (area-%) of each compound in the product stream was determined by GC-MS. Each peak was integrated (https://goldbook.iupac.org/html/P/P04453.html) and the relative amount (area-%) was obtained by comparing the area of a single peak to the sum of the peaks in the GC-MS chromatogram.

As the skilled person understands, depending on the process conditions inside the reactor, distribution of the compounds between liquid and gas phase may vary. For example GVL and 2-butanol may be present primarily in the liquid phase, but to some degree also in the gas phase. Similarly, lightest compounds such as methane and hydrogen, are primarily present in the gas phase.

In an embodiment the feedstock contains at least 80 wt-% GVL. High GVL content of the feedstock is advantageous to provide a catalytic reaction process, which proceeds efficiently from GVL as the stating material to reaction products, in particular 2-butanol. The remaining part of the feedstock may contain water, levulinic acid, pentanoic acid, furfural, and/or sulphuric acid. Thus, the process can be used to process GVL-containing feed which contains further substances in addition to GVL.

In an embodiment the process conditions provide 2-butanol in a liquid phase, wherein the ratio of 2-butanol to 2-methyltetrahydrofuran is at least 2 analysed as GC-MS area-%. In another embodiment the ratio of 2-butanol to 2-methyltetrahydrofuran is at least 2.0, 2.5, 3, 3.5, 4, 4.5, 5, 5.5 or 6 analysed as GC-MS area-%. Thus, the process can advantageously be used to produce high amount of 2-butanol. This can be achieved by selection of the catalyst and reaction conditions, such as temperature. Suitable reaction conditions can be selected by preferring process conditions that drive the reaction into the direction of 2-butanol production instead of 2-MTHF in Scheme 1.

In an embodiment the process conditions provide 2-butanol in a liquid phase, and wherein the liquid phase comprises GVL, 2-butanol, 2-methyltetrahydrofuran and pentanol such as 1-pentanol or 2-pentanol.

In an embodiment the liquid phase contains less than 80 GC-MS area-% GVL, preferably less than 80, 70, 60, 50, 40, 30 or 25 GC-MS area-% GVL.

In an embodiment the liquid phase contains at least 15 GC-MS area-% 2-butanol.

In an embodiment the liquid phase contains at least 10 GC-MS area-% 2-butanol, preferably at least 10, 15, 20, 25, 30, 40, 50, 55 or 60 GC-MS area-% 2-butanol.

In an embodiment the liquid phase contains 3-15 GC-MS area-% 2-MTHF, preferably 3-8, 4-6, 4-10, 5-15, 5-10, 6-11, 7-11, 7-10, or less than 15, less than 10, less than 8, less than 6 or less than 5 GC-MS area-% 2-2-MTHF.

In an embodiment the liquid phase contains 2-8 GC-MS area-% 1-/2-pentanol, preferably 2-7 or 2.5-6.5 GC-MS area-% 1-/2-pentanol.

In an embodiment the catalyst comprises Rh, Ru, or a combination thereof.

An advantage of having Ru and/or Rh in the catalyst is high selectivity and yield of 2-butanol production.

In an embodiment the catalyst is provided on a support. In another embodiment the support is a solid porous support. This has an advantage of improved availability of the catalytically active metal by its dispersion on a porous solid material. Further, porous support may improve activity and selectivity of the catalyst.

In an embodiment the support comprises Zr oxide, Al oxide, Ti oxide, silica, or a combination thereof.

In an embodiment the catalyst comprises $Rh/ZrO_2$ or $Ru/ZrO_2$, or a combination thereof. This has an advantage of high selectivity and yield.

In an embodiment the temperature is maintained in the range 215-270° C. during production of 2-butanol. In a preferred embodiment the temperature is maintained in the range 220-255° C. In this temperature 2-butanol production pathway is preferred (see Scheme 1).

In an embodiment the temperature is maintained in the range 240-260° C. during production of 2-butanol. In this temperature 2-butanol production pathway is even more preferred.

In an embodiment the temperature is maintained at the selected range by cooling and heating the feedstock containing GVL. Optionally the temperature of the reactor is controlled by heat transfer by conduction, preferably through reactor walls. In another embodiment, or in addition to the above means, the temperature is controlled by diluting the feedstock. As the skilled person knows, hydrogenation is typically an exothermic reaction, and temperature rise inside the reactor can be controlled by diluting the feedstock, which slows down the reaction and the resulting heat.

In an embodiment the liquid phase comprises 2-butanol, 2-methyltetrahydrofuran, 2-pentanol, 1-pentanol, 2-butanone, pentanoic acid 2-penten-1-ylester, pentanoic acid pentylester.

The inventors found that lower reaction temperature results into lower yield of 2-butanol with higher selectivity, whereas a higher temperature results into higher yield of 2-butanol and other reaction products. Thus, a higher temperature can be used to increase yield of 2-butanol, to produce further reaction products and to convert more GVL into reaction products. Accordingly, a lower reaction temperature can be selected to obtain a more selective 2-butanol production and less other reaction products.

In an embodiment the feedstock containing GVL is heated to a temperature in the range 200-300° C., preferably in the range 215-235, 220-230, 240-260, or 245-255° C., or about 225 or 250° C.

In an embodiment the temperature is maintained in the range 215-235, 220-230, 240-260, or 245-255° C., or about 225 or 250° C.

In a preferred embodiment the temperature is maintained at 220-230° C., more preferably at about 225° C. In this temperature the process provides a liquid phase containing GVL, 2-butanol, 2-methyltetrahydrofuran and 2-pentanol.

In a preferred embodiment the temperature is maintained at 245-255° C., more preferably at about 250° C. In this temperature the process provides a liquid phase containing 2-butanol, 2-methyltetrahydrofuran, 2-pentanol, 1-pentanol, 2-butanone, pentanoic acid 2-penten-1-ylester, and pentanoic acid pentylester.

In an embodiment a pressure selected from the range 40-100 bar, preferably 50-90 bar, is maintained inside the reactor during production of 2-butanol. In another embodiment a pressure of 70-90 bar, 75-85 or about 80 bar is maintained inside the reactor.

In an embodiment the process is a continuous process. Compared to batch processes, such as laboratory scale batch processes, carrying out the present invention as a continuous process is advantageous. For example, the temperature of the process can be controlled by controlling the temperature of the feed which enters the reactor.

In an embodiment the present process is carried out without adding further solvents.

In an embodiment the present process is carried out without adding water, i.e. it is a "dry process". In previous processes water has been identified as essential component to achieve selectivity to 2-butanol production. Surprisingly, the present process was selective for 2-butanol.

In an embodiment the process is a continuous flow process and the reactor is a fixed bed reactor.

In an embodiment the selectivity is determined by determining the relative amount (area-%) of each compound in the product stream by GC-MS, integrating each peak, and comparing the area of a single peak to the sum of the peaks in the GC-MS chromatogram.

In an embodiment the reaction mixture contains at least 25 GC-MS area-% GVL.

In an embodiment at least part of the unreacted GVL present in the liquid phase is recycled into the reactor. This has an advantage of higher total conversion of GVL, resulting into improved efficiency of the process.

In an embodiment the liquid phase contains at least 15% 2-butanol analysed as GC-MS area-%.

In an embodiment the pressure inside the reactor is controlled, and methane formed during the process is converted to hydrogen gas. With the combined production of hydrogen gas the total conversion of GVL into reaction product is improved, thus improving efficiency of the process.

In an embodiment methane formed in the process is conducted outside the reactor through an outlet in the reactor wall, and conversion into hydrogen is carried out in a further conversion unit. In an embodiment the further conversion unit is in fluid connection with the reactor via at least one piping, such as a discharge piping for removing fluid from the reactor, and optionally via inlet piping for loading fluids into the reactor.

In an embodiment at least part of the hydrogen gas obtained from methane is recycled to the reactor. In an embodiment the hydrogen gas is purified before feeding into the reactor.

An advantage of obtaining methane and converting it to hydrogen gas is improved process economy.

In an embodiment at least one further reaction product selected from 2-MTHF, 2-butanone, and pentyl pentanoate is recovered.

Recovery of said further reaction products is advantageous because they can be used e.g. in manufacturing of solvents and flavouring agents.

In an embodiment GVL is derived from a lignocellulosic source.

An advantage of using GVL from a lignocellulosic source is that the produced 2-butanol is produced from a renewable source. Thus, problems relating to fossil feedstocks can be avoided.

In an embodiment the reaction product is at least one of 2-MTHF, 2-butanone, and pentyl pentanoate.

In an embodiment the process comprises a further step of distilling and/or extracting the liquid phase to fractionate 2-butanol and other components.

In an embodiment the amount of metal in the catalyst is less than 5 wt-%. In another embodiment the amount of metal in catalyst is less than 4 wt-%, 3 wt-%, 2 wt-%, 1 wt-% or 0.5 wt-%, preferably about 1 wt-%.

In an embodiment the reactor is operated in a continuous mode.

In an embodiment the reactor is a fixed bed reactor

In an embodiment 2-butanol is recovered from the reactor in liquid phase.

In an embodiment the process involves a step of separating a gas phase from a liquid phase. In an embodiment the gas phase is separated from the liquid phase to separate reaction products.

In an embodiment reaction products are recovered from the reactor by conducting them into a product container. In an embodiment the product container is kept at an atmospheric pressure. In another embodiment the pressure of the reaction product feed from the reactor is reduced in a controlled manner before feeding into the product container, and gas-liquid separation is carried out to the reaction product feed before storing in the product container. Preferably light co-products in the gas phase and optionally in the liquid phase are stored in a cooled product container.

In an embodiment at least part of the gas phase obtained during gas-liquid separation is recovered. In another embodiment selected co-products present in the gas phase are recovered by condensation In an embodiment $H_2$/feed ratio is about 2000. In another embodiment the ratio is about 100-2000, preferably about 200-1000.

The $H_2$/feed can be calculated as follows: $H_2$/feed ratio (NL/L)=$H_2$ flow rate (NL/h)/GVL flow rate (ml/h)×1000

In an embodiment the liquid phase contains pentanoic acid 2-penten-1-ylester, 2-pentanol, pentanoic acid pentylester, 1-pentanol, 2-butanone, 2-butanol, 2-MTHF and GVL.

In an embodiment at least part of the 2-butanol produced in the process is used to manufacture chemicals, fuels or fuel blends.

Thus, with the present process using GVL derived from lignocellulosic source it is possible to obtain a renewable source of 2-butanol and co-products.

In an embodiment the process is carried out at an industrial scale.

In an embodiment the steps a-c of the present process are carried out in the said sequence.

EXAMPLES

The following examples are provided to illustrate various aspects of the present invention. They are not intended to limit the invention, which is defined by the accompanying claims.

Example 1—Production of 2-Butanol from GVL Over Rh/$ZrO_2$ and Ru/$ZrO_2$ Catalysts Catalyst Preparation The Ru/$ZrO_2$ and Rh/$ZrO_2$ catalysts were prepared using $RuCl_3*nH_2O$ and $Rh(NO_3)_3$, respectively, as metal precursors. The $ZrO_2$ support material was ground and sieved to the target particle size of 0.125-0.180 mm and calcined at 600° C. The metal precursor was added by incipient wetness impregnation on the support and then dried at 100° C. overnight and calcined in air at 450° C. for 2 hours. The metal contents measured for the final catalysts were 0.85 wt-% Ru and 0.86 wt-% Rh.

The hydrogenation of GVL over Rh/$ZrO_2$ and Ru/$ZrO_2$ was conducted in continuous flow fixed bed reactors. Five grams of catalyst was packed in the reactor without any inert material dilution. Commercial γ-valerolactone (Sigma-Aldrich ≥99%) was used as received without any dilution. The catalysts were dried under nitrogen flow (10 l/h) at 120° C. for 1 hour. Heating rate was 0.5° C./min. After drying, hydrogen flow was adjusted to 10 l/h and pressure was increased to 15 bar. The catalysts were reduced at 400° C.

for 5 hours. Heating rate was 3° C./min. After cooling down and soaking of the catalyst at 100° C., test conditions were adjusted to WHSV 0.5 h-1, H$_2$/feed ratio 2000 NL/L and pressure 80 bar. Only the temperature was varied during the hydrogenation experiment.

Reaction Conditions and Test Procedure

The reaction conditions used in the experiments are shown in Table 1.

TABLE 1

Reaction conditions for the preparation of 2-butanol from GVL (the density of GVL used was 1.0259 g/cm$^3$ (50° C.).

| Reaction condition | Unit | Value |
|---|---|---|
| Temperature | ° C. | 225 and 250 |
| Pressure | bar | 80 |
| Catalyst amount | g | 5 |
| GVL feed rate | g/h | 2.5 |
|  | ml/h | 2.44 |
| WHSV | 1/h | 0.5 |
| H$_2$ flow rate | g/h | 0.43 |
|  | NL/h | 4.8 |
| H$_2$/feed ratio | NL/L | ~2000 |

GVL feed rate (ml/h) = GVL feed rate (g/h)/GVL density (1.0259 g/cm$^3$) Weight-hourly-space-velocity is the mass flow rate of the reactants divided by the mass of the catalyst in the reactor,
WHSV (1/h) = GVL flow rate (g/h)/Catalyst amount (g)
H$_2$ flow rate (g/h) = H$_2$ flow rate (NL/h)/22.41 (L/mol) × molecular weight H$_2$ (g/mol)
H$_2$/feed ratio (NL/L) = H$_2$ flow rate (NL/h)/GVL flow rate (ml/h) × 1000

Example 2—Sample Analysis

The product distributions obtained in GVL hydrogenation over Rh/ZrO$_2$ and Ru/ZrO$_2$ catalysts at 225 and 250° C. are shown in FIGS. 1A and 1B and in Table 2.

According to GC-MS results the GVL conversion as well as the 2-butanol yield increased when the hydrogenation temperature increased from 225 to 250° C.

The liquid product stream obtained in the hydrogenation experiment was analysed with offline Gas Chromatography-Mass Spectrometry, GC-MS (Agilent GC 6890A mit MSD 5973). Peaks in the GC chromatogram were assigned to various compounds by MS. The relative amount (area-%) of each compound in the product stream was determined by GC-MS. Each peak was integrated (https://goldbook.iupac.org/html/P/P04453.html) and the relative amount (area-%) was obtained by comparing the area of a single peak to the sum of the peaks in the GC-MS chromatogram. The amount of GVL (wt-%) was determined quantitatively with GC-FID from response factor that was calibrated with pure GVL.

Gas Chromatography-Flame Ionization Detector or GC-FID is a very common analytical technique that is widely used in the petrochemical, pharmaceutical and natural gas markets.

An FID typically uses a Hydrogen/Air flame into which the sample is passed to oxidise organic molecules and produces electrically charged particles (ions). The ions are collected and produce an electrical signal which is then measured.

The conversion of GVL calculated from the quantitative amount of GVL remaining in the product was 50.5 and 69.8 wt-% for Rh/ZrO$_2$ at 225 and 250° C., respectively, and 42.8 and 78.7 wt-% for Ru/ZrO$_2$ at 225 and 250° C., respectively.

TABLE 2

Product distribution, 2-butanol selectivity and 2-butanol-to-MTHF-ratio in organic liquid phases obtained at 225 and 250° C. with Rh/ZrO$_2$ and Ru/ZrO$_2$ catalysts (in GC area-%).

|  |  | Rh/ZrO$_2$ at 225° C. | Rh/ZrO$_2$ at 250° C. | Ru/ZrO$_2$ at 225° C. | Ru/ZrO$_2$ at 250° C. |
|---|---|---|---|---|---|
| GVL | area-% | 75.4 | 58.0 | 69.1 | 29.1 |
| 2-MTHF | area-% | 5.7 | 4.8 | 7.6 | 9.5 |
| 2-Butanol | area-% | 16.1 | 25.7 | 20.7 | 51.2 |
| 1-/2-Pentanol | area-% | 2.8 | 4.8 | 2.6 | 6.2 |
| Butanone | area-% | — | 1.6 | — | 3.3 |
| Esters | area-% | — | 3.6 | — | — |
| Other minor | area-% | — | 0.55 | — | 0.79 |
| Unknowns | area-% | — | 0.97 | — | — |
| 2-Butanol selectivity | area-% | 65.4 | 61.2 | 67.0 | 72.2 |
| 2-Butanol-to-MTHF-ratio | area-% | 2.8 | 5.4 | 2.7 | 5.4 |

High selectivity for 2-butanol was achieved in the hydrogenation reactions carried out at 225-250° C. and 80 bar. At these temperatures the selectivity for 2-butanol over Rh/ZrO$_2$ was 61-65 area-% and over Ru/ZrO$_2$ 67-72 area-%. The selectivity obtained in these reactions is highly improved compared to 2-butanol selectivity values found in the literature for GVL hydrogenation. For example, Al-Shaal et al. (Green Chem., 2014, 16, 1358) have reported the formation of mainly 2-MTHF and 2-butanol at 190° C. and 100 bar when using 5 wt-% Ru/C as GVL hydrogenation metal. At the highest GVL conversion reported almost equal amounts of 2-MTHF (43%) and 2-butanol (36%) were obtained (with a butanol-to-MTHF-ratio of 0.8). Based on the 2-butanol-to-MTHF-ratios (=2.7-5.4) of the Rh/ZrO$_2$ and Ru/ZrO$_2$ catalysts it is proposed that the reaction route giving 2-butanol is preferred over the route leading to 2-MTHF. Further, with said catalysts, it is possible to direct the catalytic process to higher selectivity for 2-butanol, or higher yield of 2-butanol, simply by changing temperature. For the Ru/C catalyst with a 2-butanol-to-MTHF-ratio of 0.8, both routes are proposed to occur with almost equal probability and no selectivity is obtained.

As the examples indicate, in the present invention highly improved selectivities for 2-butanol formation from GVL was achieved. In particular Rh/ZrO$_2$ and Ru/ZrO$_2$ catalysts were superior in selectivity compared to selectivity values reported in the literature (e.g. over 5 wt-% Ru/C). In the present invention a much lower amount of catalyst, i.e. 1 wt-% Rh/ZrO$_2$ and Ru/ZrO$_2$, was sufficient to achieve high selectivity and yield of the 2-butanol production.

Different non-binding example aspects and embodiments of the present invention have been illustrated in the foregoing. The embodiments are used merely to explain selected aspects or steps that may be utilized when implementing the present invention. Some embodiments may be presented herein only with a reference to a certain aspect of the invention. It should be appreciated that the embodiments may apply to other aspects of the present invention, as well. Consequently, any appropriate combination of the embodiments and the aspects may be formed. Any combination of aspects or embodiments as disclosed herein may also be made without at least one non-essential feature disclosed in an aspect or embodiment.

The invention claimed is:
1. A process for selective production of 2-butanol from γ-valerolactone (GVL), the process comprising:

a. providing in a reactor at least one transition metal catalyst selected from a group consisting of iron, ruthenium, cobalt, rhodium and iridium;
b. heating a feedstock containing GVL, thereby forming a heated GVL feedstock;
c. forming a reaction mixture by feeding into the reactor:
   i. the heated GVL feedstock; and
   ii. hydrogen gas; and
d. maintaining a temperature of the reaction mixture in a range of 200–300° C. to allow selective production of reaction products containing 2-butanol,
wherein no water is fed into the reactor during the process.

2. The process of claim 1, wherein the selectivity of 2-butanol production is at least 50% analysed as GC-MS area-%.

3. The process of claim 1, wherein the feedstock contains at least 80 wt-% GVL.

4. The process of claim 1, wherein in the process conditions provide 2-butanol in a liquid phase, wherein a ratio of 2-butanol to 2-methyltetrahydrofuran is at least 2 analysed as GC-MS area-%.

5. The process of claim 1, wherein the catalyst comprises: Rh, Ru, or a combination thereof.

6. The process of claim 1, wherein the catalyst is provided on a support.

7. The process of claim 6, wherein the support comprises: Zr oxide, Al oxide, Ti oxide, silica, or a combination thereof.

8. The process of claim 1, wherein the catalyst comprises: Rh/ZrO2 or Ru/ZrO2, or a combination thereof.

9. The process of claim 1, wherein the temperature is maintained in a range 215-270° C. during production of 2-butanol.

10. The process of claim 1, wherein the temperature is maintained in a range 240-260° C. during production of 2-butanol.

11. The process of claim 1, wherein in the process conditions provide 2-butanol in a liquid phase, and wherein the liquid phase comprises:
GVL, 2-butanol, 2-methyltetrahydrofuran and 2-pentanol.

12. The process of claim 11, wherein the liquid phase comprises:
2-butanol, 2-methyltetrahydrofuran, 2-pentanol, 1-pentanol, 2-butanone, pentanoic acid 2-penten-1-ylester, and pentanoic acid pentylester.

13. The process of claim 1, wherein a pressure selected from a range of 40-100 bar, or a range of 50-90 bar, is maintained inside the reactor during production of 2-butanol.

14. The process of claim 1, wherein the process is a continuous process.

15. The process of claim 14 wherein at least part of a unreacted GVL present in the liquid phase is recycled into the reactor.

16. The process of claim 1, wherein the liquid phase contains at least 15% 2-butanol analysed as GC-MS area-%.

17. The process of claim 1, comprising:
controlling pressure inside the reactor, and converting methane formed during the process to hydrogen gas.

18. The process of claim 1, comprising:
recovering at least one further reaction product selected from 2-MTHF, 2-butanone, and pentyl pentanoate.

19. The process of claim 1, wherein GVL is derived from a lignocellulosic source.

20. A method comprising:
applying a catalyst containing at least one transition metal selected from a group consisting of iron, ruthenium, cobalt, rhodium and iridium, in a selective production of 2-butanol from GVL, wherein no water is fed into the method during the selective production of 2-butanol from GVL.

* * * * *